United States Patent [19]
Wiley

[11] Patent Number: 5,489,291
[45] Date of Patent: Feb. 6, 1996

[54] APPARATUS FOR REMOVING TISSUE DURING SURGICAL PROCEDURES

[76] Inventor: Roy C. Wiley, 73 S. C.R. 325 E., Warsaw, Ind. 46580

[21] Appl. No.: 200,397

[22] Filed: Feb. 23, 1994

[51] Int. Cl.$^6$ .................................................. A61B 17/32
[52] U.S. Cl. ......................... 606/170; 606/171; 606/180; 604/22
[58] Field of Search ..................................... 606/167, 170, 606/171, 180, 159; 604/22; 128/750–755

[56] References Cited

U.S. PATENT DOCUMENTS

| | | | |
|---|---|---|---|
| 4,445,509 | 5/1984 | Auth | 606/180 |
| 5,100,426 | 3/1992 | Nixon | 604/22 |
| 5,217,479 | 6/1993 | Shuler | 606/180 |
| 5,269,794 | 12/1993 | Rexroth | 606/180 |

FOREIGN PATENT DOCUMENTS

| | | | |
|---|---|---|---|
| 9215255 | 9/1992 | WIPO | 604/22 |

*Primary Examiner*—Stephen C. Pellegrino
*Assistant Examiner*—William W. Lewis
*Attorney, Agent, or Firm*—Harness, Dickey & Pierce

[57] ABSTRACT

An apparatus for removing tissue from a surgical site during a surgical procedure. The apparatus includes an abrading element for abrading the tissue during the surgical procedure. The abrading element has an abrading surface and at least one aperture disposed on the abrading surface. The apparatus also includes a shaft for supporting the abrading element during the surgical procedure as well as to permit rotation of the abrading element.

13 Claims, 3 Drawing Sheets

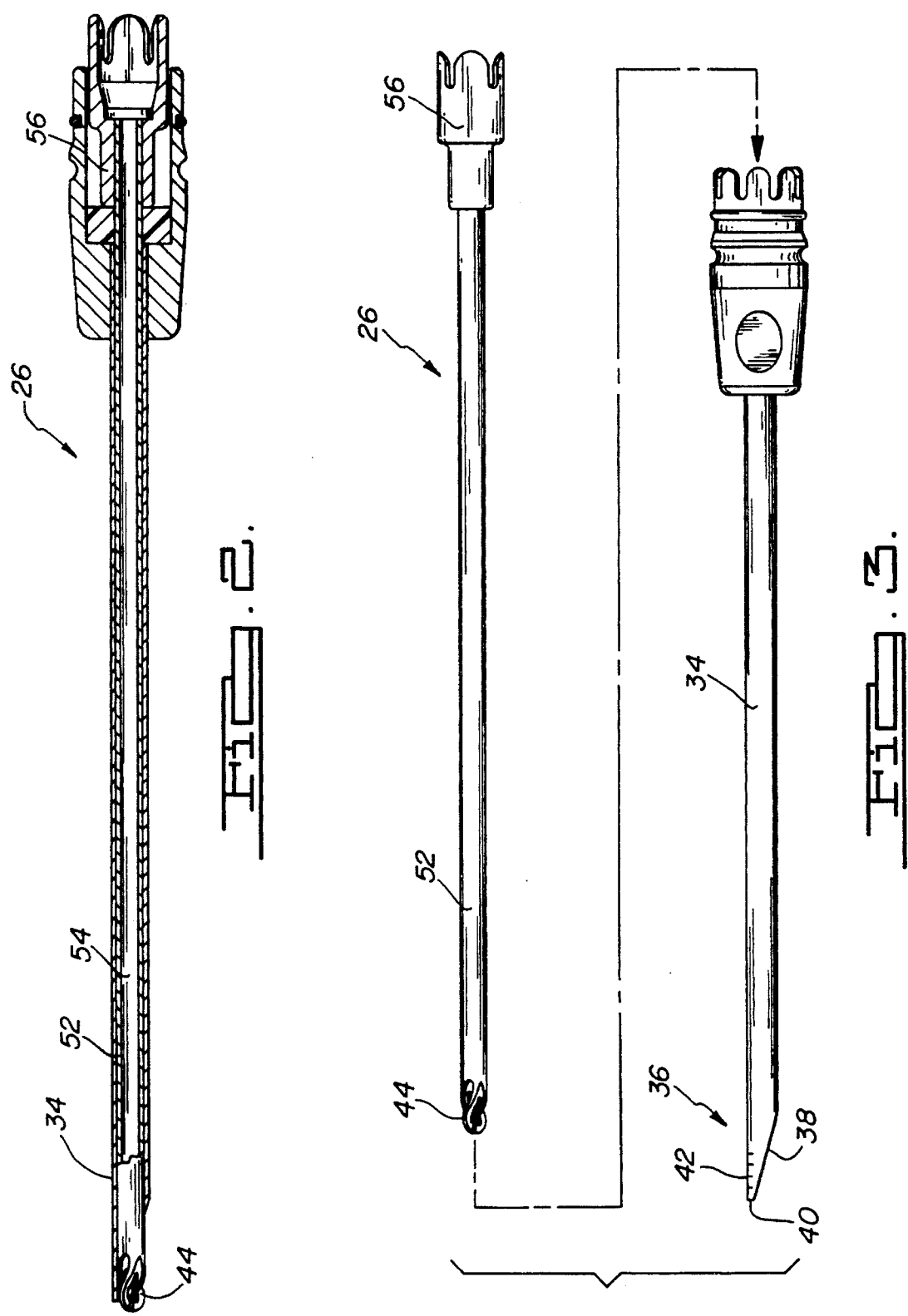

APPARATUS FOR REMOVING TISSUE DURING SURGICAL PROCEDURES

BACKGROUND OF THE INVENTION

1. Field of the Invention

This invention relates to removal of tissue during surgical procedures in a minimally invasive manner, and more particularly to a method and apparatus for abrasion and removal of bone, cartilage, and other tissues during surgical procedures.

2. Description of the Related Art

During various types of surgical procedures, it is often desirable to remove tissue in the least invasive manner in the interest of patient safety, recovery time, and wound healing. In certain arthroscopic procedures, for example, degenerated or hypertrophic cartilage on joint surfaces is abraded, exposing small underlying capillaries that foster regrowth of healthy cartilage. In this manner, cartilage within a diseased joint space is encouraged to regrow thereby promoting restoration of a functional joint. The alternative method of total joint replacement by surgical procedure is more invasive requiring more post-operative recovery time.

In the arthroscopic procedures that are relatively non-invasive, a surgical instrument is introduced through the skin and into a surgical site. The location of the surgical instrument within the surgical site is monitored by an arthroscopic visualization apparatus. With the aid of this visualization apparatus, the surgeon guides the surgical instrument to the diseased joint surface where the surgeon begins to remove the diseased surface. Suction through another device adjacent to the surgical instrument or through the surgical instrument itself removes the tissue abraded by the surgical instrument along with surrounding tissue fluid or fluid introduced to the tissue area by various means.

Because of the decided advantages of the non-invasive arthroscopic procedures, a variety of surgical instruments have been developed which are used for such procedures. Such surgical instruments ordinarily feature either an abrading element or a cutting element. These surgical instruments also ordinarily require the use of an arthroscopic visualization apparatus for monitoring the progression of the surgical instrument through the tissues to the surgical site and for monitoring the cutting or the abrading of the joint surface.

One such surgical instrument is disclosed in U.S. Pat. No. 4,842,578. This reference describes an abrading instrument that includes the combination of a distally, side-supported inner shaft carrying on its end an abrading element, and a fixed outer tubular member surrounding the inner shaft and providing support for the inner shaft. The abrading element is shielded along one side, while another side and the end of the element are exposed for abrading action. This surgical instrument also includes a passageway for removing fluid and severed tissue.

Although the surgical instrument described in the above reference features a distal entry way for fluid to enter the instrument from the surgical site by suction, the fluid does not enter directly through the abrading element. Rather, fluid is drawn by suction across the exterior of the abrading element and into an annular cavity between the distal and proximal portions of the outer tubular member. From there the fluid being removed from the surgical site must pass through a suction port and through a distal bearing and into a conduit formed by the inner shaft. From the inner shaft, the fluid passes through a proximal bearing and into a sluff chamber which is connected to a vacuum source. Such circuitous travel by the suctioned fluid decreases the suction force upon the edge of the abrading element and increases the likelihood that tissue particles will be trapped within the instrument. In addition, because the suction port rotates with respect to the outer tubular member, the suction port is restricted by the outer tubular member as the inner shaft rotates.

The present invention has as a primary objective the provision of a surgical abrader capable of end abrading as well as side abrading and that provides an aperture in the abrading element so that steady aspiration of abraded tissues is achieved and that the tissue is effectively removed through the end of the abrading element.

SUMMARY OF THE INVENTION

In one embodiment, the present invention relates to an apparatus for removing tissue from a patient during a surgical procedure. The apparatus includes means for abrading the tissue from the patient during the surgical procedure. The means for abrading the tissue include an abrading surface with at least one aperture disposed in the abrading surface. In addition, the apparatus also includes means for providing support to the means for abrading during the surgical procedure.

In another embodiment, the present invention relates to an apparatus for abrading tissue from a patient during a surgical procedure. The apparatus includes a surgical instrument having an outer sleeve for introduction of the surgical instrument into the patient. The surgical instrument also includes an abrading element with apertures for abrading and removing tissue. The surgical instrument further includes an inner shaft for removing fluid and severed tissue from the apertures in the abrading element through the surgical instrument. The inner shaft is rotatable and carries the abrading element on its distal end. In addition to the surgical instrument, the apparatus also includes means for rotating the inner shaft to provide the abrading surface with an abrading action as the inner abrading element rotates. Finally, the apparatus includes means for applying a vacuum to the surgical instrument so as to draw fluid and abraded tissue through the abrading surface and the inner shaft to a position remote from the surgical site.

In yet another embodiment, the present invention also relates to a method for abrading and removing cartilage, bone, and other tissues during surgical procedures such as in arthroscopy. The method includes the initial step of forming an apparatus for abrading cartilage and bone within a surgical site. The apparatus includes a surgical instrument having an inner shaft for suctioning severed cartilage and bone through at least one aperture in the abrading surface of the surgical instrument. The method also includes introducing the surgical instrument into the surgical site and then rotating the inner shaft so that the edges on the abrading surface abrade the tissue, cartilage, or bone. The method finally includes aspirating the abraded tissue, cartilage, or bone through a flow passage in the inner shaft and out of the surgical site.

The present invention is especially useful for procedures such as arthroscopy, wherein the surgical instrument can be introduced through the skin and, with the assistance of an arthroscopic visualization apparatus, can be advanced through the tissues underlying the skin to cartilage and bone on joint surfaces within a joint cavity. The surgical instrument can then be used to abrade damaged cartilage and bone on the joint surfaces. The surgical instrument can be attached to a suctioning device so that surrounding fluid and the abraded tissues can be suctioned directly away from the site.

An advantage of the present invention is to provide a method and apparatus for abrading tissue during a surgical procedure in which fluid and severed tissue are drawn through the abrading surface of a surgical instrument and directly through an inner shaft supporting the abrading surface.

Another advantage of the present invention is to provide a method and apparatus for abrading tissue during a surgical procedure which is relatively simple to use, is non-invasive, allows optimum suctioning of abraded tissue, and is adaptable to a variety of patients as well as a variety of surgical procedures.

A further advantage of the present invention is to provide a method and apparatus for abrading tissue during a surgical procedure whereby the flow of the fluid through the instrument used to remove the tissue is relatively unimpeded.

An additional advantage of the present invention is to provide a method and apparatus for abrading tissue during a surgical procedure in which the flow passage for abraded tissue is not restricted by an outer tubular member.

Another advantage of the present invention is to provide a method and apparatus for surgical repair of diseased and degenerated joint surfaces with minimal invasiveness and therefore with minimal risk to the patient.

BRIEF DESCRIPTION OF THE DRAWINGS

Various advantages of the present invention will become apparent to one skilled in the art upon reading the following specification and reference to the following drawings in which:

FIG. 2 is a longitudinal partial cross-sectional view of the surgical instrument used for abrading tissue during a surgical procedure shown in FIG. 1 according to the first preferred embodiment of the present invention;

FIG. 3 is an exploded elevational view of the surgical instrument used for abrading tissue during a surgical procedure according to the first preferred embodiment of the present invention shown in FIG. 1;

DISCUSSION OF THE PREFERRED EMBODIMENTS

The following discussion of the preferred embodiments of the present invention is merely exemplary in nature. Accordingly, the discussion is in no way intended to limit the scope of the invention, the application of the invention, or the use of the invention.

Figure 1:
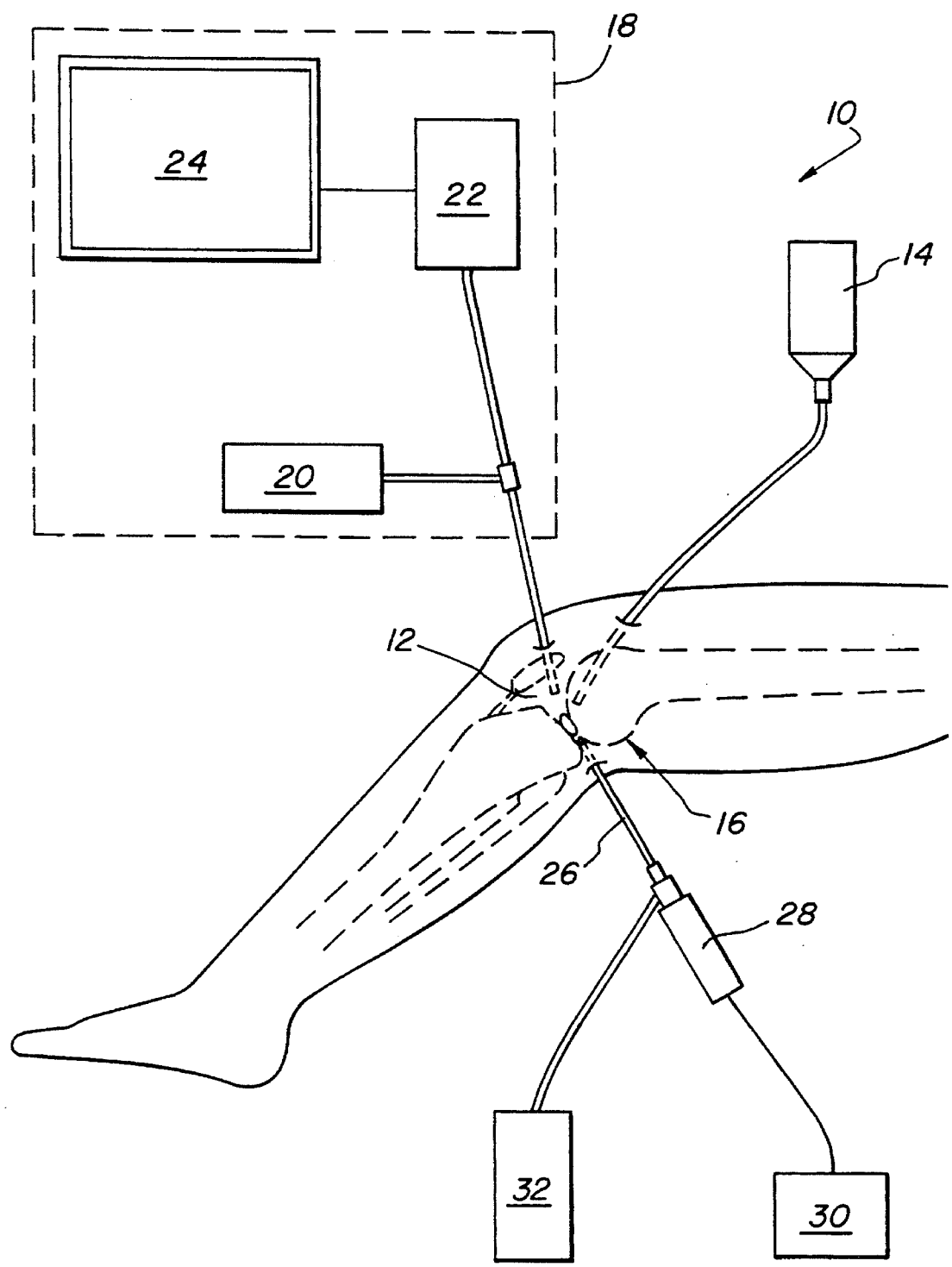
FIG. 1 is a diagrammatic illustration of the apparatus for abrading tissue during surgical procedures shown in operative association with a tibia and femur according to the preferred embodiments of the present invention.
Figure 4:
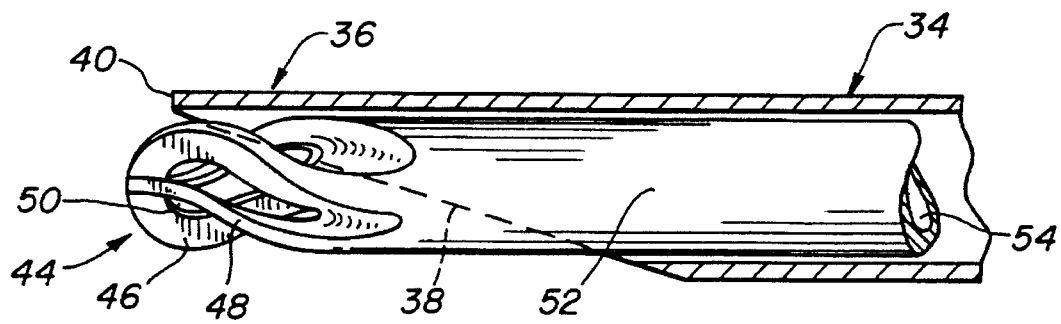
FIG. 4 is an enlarged longitudinal partial cross-sectional view of the distal end of the surgical instrument used for abrading tissue during a surgical procedure shown in FIG. 2 according to the first preferred embodiment of the present invention.

Referring to FIG. 1, an apparatus for abrading tissue during surgical procedures is shown and is generally designated by the numeral 10. The apparatus 10 may be used, for example, during abrasion and removal of tissue such as cartilage and bone within the surgical site 12. The apparatus 10 includes a source 14 of sterile fluid such as saline which is provided to the surgical site 12 so as to distend the joint 16 and provide a sterile wash to the abraded tissue. The apparatus 10 also includes a fiber optic visualization instrument 18 which provides light to the surgical site 12 by means of a light source 20 and returns an image of the surgical site 12 by means of a camera 22. The image which is received by the camera 22 is in turn displayed upon screen 24 or returned to the surgeon by other means, such as through an eye piece worn by the surgeon. Guided by the image, the surgeon can move a surgical instrument 26 within the surgical site 12 during removal or abrading of the tissue from the joint 16. The apparatus 10 also includes a hand held rotary power source 28 which is used to rotate the surgical instrument 26 when the surgical instrument 26 is in the surgical site 12. The rotary power source 28 may in turn be controlled by the surgeon using a foot pedal 30. Finally, the apparatus 10 may also include a vacuum source 32 which is connected to the surgical instrument 26 for providing a vacuum for withdrawal of abraded tissue from the surgical site 12.

As will be appreciated by those skilled in the art, the apparatus 10 may be used in a variety of surgical procedures including but not limited to abrasion and evacuation of fatty or diseased tissue from the body, as for example in liposuction or in surgical debridement or in removal of tumors. Further, the apparatus 10 may be used in the removal of bony protrusions such as bone spurs or vertebral protrusions. In addition, the apparatus 10 also allows for the insertion of a sterile catheter for delivery of sterile fluid including but not limited to antibiotic fluid to tissue in the joint 16. While some of the components of the apparatus 10 described above may preferably be part of a Model IES 1000 available from Arthrotek, Ontario, Calif., other suitable arthroscopic devices may be used.

A surgical instrument 26 of the present invention will now be described with reference to FIGS. 2–7. The surgical instrument 26 is operable to abrade tissue within the surgical site 12 as well as withdraw the abraded tissue from the surgical site 12. As will be more fully described below, the path through which abraded tissue flows through the surgical instrument 26 is substantially direct and unimpeded so as to minimize the resistance to flow of the abraded tissue through the surgical instrument 26. This in turn increases the suction force which can be applied by the surgical instrument 26 as well as decreases the possibility that particles of abraded tissue may be trapped within the surgical instrument 26.

To provide means for introducing the surgical instrument 26 into the surgical site, the surgical instrument 26 includes an outer sleeve 34 which is substantially cylindrical in configuration. The outer sleeve 34 includes a substantially fully open distal end 36 which is defined by a generally conical tapered section 38 at its proximal end and a generally part-spherical section 40 at its distal end. On the exterior surface of the conical section 38 are a plurality of indentations 42 which are used as depth measuring indications when surgery is being performed. The generally conical tapered section 38 may also include a plurality of teeth which are used for severing tissue which is brought adjacent to the conical section 38 by the abrading element described below. While the outer sleeve 34 is preferably made from stainless steel, it will be understood that any other suitable material may be used.

To provide means for abrading tissue during the surgical procedure, the surgical instrument 26 further comprises an abrading element 44. The abrading element 44 is generally cylindrical in shape and includes an abrading surface 46 which has a plurality of abrading ridges 48 disposed thereon. The ridges 48 on the abrading surface 46 are operable to abrade tissue in the surgical site 12 upon engagement with the tissue. The abrading surface 46 further includes a plurality of helically oriented apertures 50 which are disposed centrally on the abrading surface 46 between the abrading ridges 48. The apertures 50 provide a path for fluid and abraded tissue to flow directly from the abrading surface 46 and into the central bore of the inner shaft which are fully described below. While the abrading surface 46 is preferably made from stainless steel, it will be understood that any other suitable material may be used.

To provide means for supporting the abrading element 44 within the outer sleeve 34, the surgical instrument 26 further includes an inner shaft 52 which is connected to the abrading element 44. The inner shaft 52 is cylindrical in shape and is rotatable within the outer sleeve 34. The inner shaft 52 includes a flow passage 54 which extends the length of the inner shaft 52. The flow passage 54 is in communication with the apertures 50 in the abrading element 44 so as to allow abraded tissue to flow from the abrading element 44 through the flow passage 54 in the inner shaft 52. Although the abrading element 44 rotates with respect to the outer sleeve 34, the presence of more than one aperture on the abrading element 44 insures that the flow of abraded tissue through the abrading element 44 is substantially uniform during rotation of the abrading element 44. That is, if a single aperture were present on the abrading element 44, the aperture would be at least partially obstructed by the outer sleeve 34 during at least part of each rotation. This in turn would tend to cause the suction applied to the surgical site 12, as well as the flow of abraded tissue through the flow passage 54, to be non uniform.

It will be appreciated that it is desirable to have the flow passage 54 formed so as to avoid the occurrence of stress risers. It is therefore desirable not to have the end of the flow passage 54 proximate to the abrading element 44 formed to have sharp surfaces. The inner shaft 52 also includes an attachment member 56 at its proximal end which is operable to be connected to the rotary power source 28 so as to allow said inner shaft 52 to rotate. While the inner shaft 52 is preferably made from stainless steel, it will be understood that any other suitable material may be used.

Figure 5:
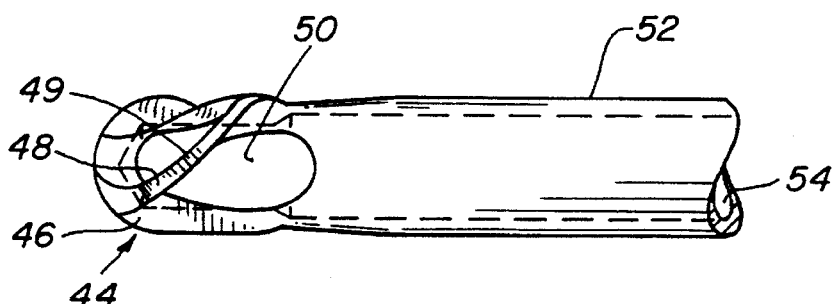
FIG. 5 is an enlarged elevational view of the abrading element shown in FIG. 2 according to the second preferred embodiment of the present invention.
Figure 6:
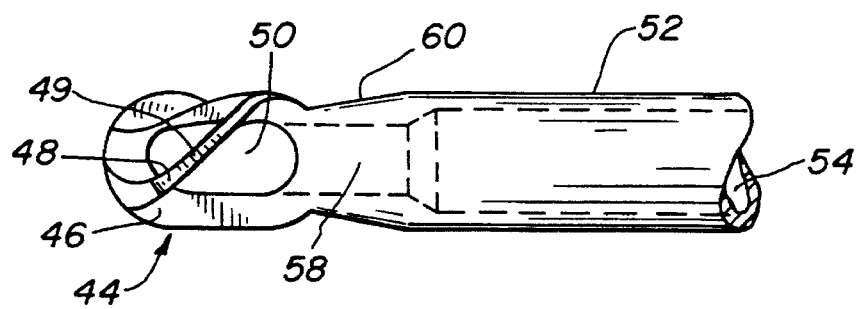
FIG. 6 is an enlarged elevational view of the abrading element shown in FIG. 2 to the third preferred embodiment of the present invention shown in FIG. 1.

The abrading element 44 and the inner shaft 52 of the surgical instrument 26 may be of different configurations. In this regard, the second and third preferred embodiments of the present invention is shown in FIGS. 5 and 6 respectively, where like numerals are used to identify similar elements as described with respect to the first preferred embodiment of the present invention. In the second preferred embodiment, the abrading ridges 48 have a plurality of chip breakers 49 which are used to assist in the abrading action of the abrading element 44. The chip breakers 49 in the third preferred embodiment of the present invention shown in FIG. 6, the flow passage 54 has a reduced portion 58 which corresponds with a tapered portion 60 of the inner shaft 52. As illustrated in FIGS. 2 and 5, the flow passage 54 includes an inner diameter that is of relatively constant width from the area immediately adjacent and slightly overlapping the helically oriented apertures 50 to the opposite end of the inner shaft 52.

Figure 7:
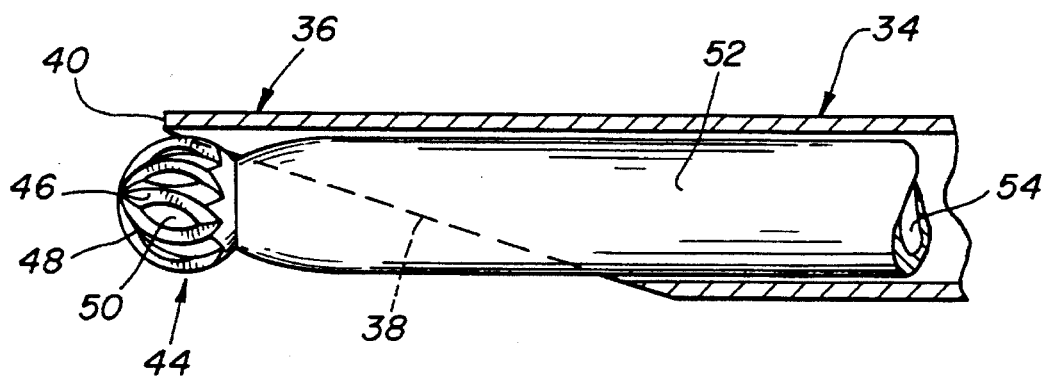
FIG. 7 is an enlarged longitudinal partial cross-sectional view of the distal end of the surgical instrument used for abrading tissue during a surgical procedure according to the fourth preferred embodiment of the present invention shown in FIG. 1.

The fourth embodiment of the present invention will now be described with reference to FIG. 7. In this regard, like numerals are used to identify similar elements as described with respect to the first preferred embodiment of the present invention. The surgical instrument 26 according to the fourth preferred embodiment of the present invention functions in a manner similar to that described with respect to the first preferred embodiment of the present invention. However, the abrading element 44 according to the fourth preferred embodiment is substantially spherical in configuration with a plurality of elongated apertures 50 concentrically disposed with respect to the center of the abrading element. The abrading element 44 is also connected to an inner shaft 52 with a flow passage 54 disposed therein. Accordingly, tissue which is abraded by the abrading element 44 is able to flow through the apertures 50 in the abrading element 44 and through the flow passage 54 in the inner shaft 52.

The method of the present invention will now be described. The surgical instrument 26 for use in abrading tissue is first formed. In this regard, the outer sleeve 34 is formed and then the abrading element 44 is formed on the distal end of the inner shaft 52. The inner shaft 52 is then inserted into the outer sleeve 34 and attached to the rotary power source 28 as well as the vacuum source 32. The surgical instrument 26 is then inserted into the surgical site 12 and then the inner shaft 52 is rotated with respect to the outer sleeve 34. As the inner shaft 52 rotates, the surface on the abrading element 44 causes abraded tissue to be severed from the remaining tissue. The abraded tissue is then removed from the surgical site 12 through the apertures 50 in the abrading element 44 and the flow passage 54 in the inner shaft 52.

Those skilled in the art can now appreciate from the foregoing that the broad teachings of the present invention can be implemented in a variety of forms. Therefore, while the invention was described in connection with particular examples hereof, the true scope of the invention should not be so limited. The present invention may be used with a variety of surgical procedures which may not necessarily involve abrasion of bone and cartilage. For example, the proximal end of the inner shaft may be fitted with an attachment to means for introducing fluids to tissues. In this manner, antibiotics or other substances can be delivered directly to tissue within the body. As another example, the present invention may be utilized for abrading and evacuating fatty or diseased tissue from the body as, for example, in liposuction or in surgical debridement or in removal of tumors. As another example, the inner shaft may carry on its distal end a sampling surface for collecting biopsies of body tissues. In addition, the abrading surface does not necessarily have to be spherical or elongated in overall configuration, but may be of other shapes which are desirable for a particular application. Other modifications will become apparent to those skilled in the art.

What is claimed is:

1. An apparatus for removing tissue from a surgical site during a surgical procedure, said apparatus comprising:
   means for abrading the tissue during the surgical procedure, said means for abrading the tissue including:
   (a) an abrading surface, said abrading surface including at least one generally helically oriented abrading ridge, and
   (b) at least one generally helically oriented aperture disposed in said abrading surface, said generally helically oriented aperture being defined adjacent said at least one generally helically oriented abrading ridge; and means for providing support to said means for abrading during the surgical procedure, said means for providing support being operable to permit rotation of said means for abrading.

2. The apparatus for removing tissue from a surgical site during a surgical procedure as set forth in claim 1, wherein said means for providing support to said means for abrading includes an inner shaft and an outer sleeve, said inner shaft being rotatable with respect to said outer sleeve.

3. The apparatus for removing tissue from a surgical site as set forth in claim 1, wherein said outer sleeve has a plurality of teeth disposed thereon, said teeth being operable to cut the tissue which is abraded by said abrading surface.

4. The apparatus for removing tissue from a surgical site during a surgical procedure as in claim 1, wherein said means for providing support to said means for abrading includes means for withdrawing abraded tissue through the aperture in said abrading surface.

5. The apparatus for removing tissue from a surgical site during a surgical procedure as in claim 4, wherein said means for withdrawing abraded tissue through the aperture in said abrading surface includes a shaft secured to said means for abrading, said shaft having a flow passage disposed therein that is in communication with the aperture in the abrading surface.

6. The apparatus for removing tissue from a surgical site during a surgical procedure as set forth in claim 1, further comprising a plurality of generally helically oriented abrading ridges and a plurality of apertures, each one of said plurality of apertures being disposed between each one of said abrading ridges.

7. The apparatus for removing tissue from a surgical site during a surgical procedure as set forth in claim 1, wherein said means for abrading the tissue during the surgical procedure includes a substantially spherical abrading element.

8. The apparatus for removing tissue from a surgical site as set forth in claim 1, wherein said abrading surface has a plurality of chip breakers disposed thereon.

9. A method for abrading tissue during a surgical procedure, said method comprising the steps of:

providing a surgical instrument for abrading tissue, said surgical instrument having:
  (a) means for abrading the tissue during the surgical procedure, said means for abrading the tissue including:
    an abrading surface, said abrading surface having at least one generally helically oriented abrading ridge, and at least one generally helically oriented aperture disposed in said abrading surface, said generally helically oriented aperture being defined adjacent said at least one helically oriented abrading ridge; and
  (b) means for providing support to said means for abrading during the surgical procedure, said means for providing support being operable to permit rotation of said means for abrading;

abrading the tissue with said surgical instrumentation;

removing the abraded tissue through the aperture in said means for abrading.

10. The method for abrading tissue during a surgical procedure as set forth in claim 9, wherein said step of providing said surgical instrument includes a surgical instrument having an inner shaft with a flow passage disposed therein.

11. The method for abrading tissue during a surgical procedure as set forth in claim 10, further comprising the additional step of removing tissue through the aperture in the abrader and through said flow passage in said inner shaft.

12. The method for abrading tissue as set forth in claim 9, wherein said step of providing a surgical instrument further includes a surgical instrument having a plurality of chip breakers on said abrading surface.

13. An apparatus for removing tissue from a surgical site during a surgical procedure, said apparatus comprising:

a surgical instrument for use in abrading the tissue, said surgical instrument including an elongated rotatable shaft, said shaft including an abrading end and a proximal end, said shaft having a substantially straight flow passage defined therein beginning adjacent said abrading end, said flow passage being of substantially constant width between said abrading end and said proximal end, said instrument further including at least one helically oriented abrading ridge and at least one helically oriented aperture defined on said abrading end, said at least one aperture being continuous with said flow passage;

means for rotating at least a portion of said surgical instrument so as to cause said surgical instrument to produce an abrading action, said means for rotating including a hand-held rotary power source having a plurality of switches disposed thereon which are operable to control the speed of rotation of said portion of said surgical instrument; and means for applying a vacuum to said surgical instrument so as to withdraw tissue which has been abraded by the surgical instrument.

* * * * *